United States Patent
Sasaki et al.

(10) Patent No.: US 12,178,814 B2
(45) Date of Patent: Dec. 31, 2024

(54) PHARMACEUTICAL COMPOSITION

(71) Applicant: ASTELLAS PHARMA INC., Tokyo (JP)

(72) Inventors: Akihiko Sasaki, Tokyo (JP); Ko Tanaka, Tokyo (JP); Masakazu Miyazaki, Tokyo (JP); Seiji Takae, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 738 days.

(21) Appl. No.: 17/441,361

(22) PCT Filed: Apr. 2, 2020

(86) PCT No.: PCT/JP2020/015225
§ 371 (c)(1),
(2) Date: Sep. 21, 2021

(87) PCT Pub. No.: WO2020/204142
PCT Pub. Date: Oct. 8, 2020

(65) Prior Publication Data
US 2022/0152020 A1  May 19, 2022

(30) Foreign Application Priority Data
Apr. 3, 2019  (JP) .................... 2019-070997

(51) Int. Cl.
*A61K 31/497* (2006.01)
*A61K 9/16* (2006.01)
*A61K 9/20* (2006.01)

(52) U.S. Cl.
CPC .......... *A61K 31/497* (2013.01); *A61K 9/1623* (2013.01); *A61K 9/2018* (2013.01)

(58) Field of Classification Search
CPC ................................... A61K 31/497
See application file for complete search history.

(56) References Cited

U.S. PATENT DOCUMENTS

| | | | |
|---|---|---|---|
| 8,969,336 B2 | 3/2015 | Shimada et al. | |
| 9,487,491 B2 | 11/2016 | Shimada et al. | |
| 10,786,500 B2 | 9/2020 | Miyazaki et al. | |
| 11,938,130 B2 | 3/2024 | Miyazaki et al. | |
| 11,938,131 B2 | 3/2024 | Miyazaki et al. | |
| 11,938,132 B2 | 3/2024 | Miyazaki et al. | |
| 11,938,133 B2 | 3/2024 | Miyazaki et al. | |
| 11,944,620 B2 | 4/2024 | Miyazaki et al. | |
| 2012/0040968 A1 | 2/2012 | Shimada et al. | |
| 2013/0150370 A1 | 6/2013 | Steckel | |
| 2013/0338238 A1 | 12/2013 | Maruyama et al. | |
| 2014/0371196 A1 | 12/2014 | Shimada et al. | |
| 2015/0141517 A1 | 5/2015 | Hirama et al. | |
| 2017/0105988 A1 | 4/2017 | Fanara et al. | |
| 2018/0110763 A1 | 4/2018 | Dutt et al. | |
| 2018/0185359 A1 | 7/2018 | Miyazaki et al. | |
| 2020/0038333 A1 | 2/2020 | Hirama et al. | |
| 2020/0383977 A1 | 12/2020 | Miyazaki et al. | |
| 2023/0129146 A1 | 4/2023 | Miyazaki et al. | |
| 2023/0277529 A1 | 9/2023 | Miyazaki et al. | |
| 2023/0277530 A1 | 9/2023 | Miyazaki et al. | |
| 2023/0277531 A1 | 9/2023 | Miyazaki et al. | |
| 2023/0277532 A1 | 9/2023 | Miyazaki et al. | |
| 2023/0301992 A1 | 9/2023 | Miyazaki et al. | |

FOREIGN PATENT DOCUMENTS

| | | |
|---|---|---|
| CN | 107847500 A | 3/2018 |
| EA | 31697 B1 | 2/2019 |
| JP | 2009-256344 A | 11/2009 |
| JP | 2014-015459 A | 1/2014 |
| JP | 2015-117240 A | 6/2015 |
| RU | 2526253 C2 | 8/2014 |
| TW | 201716069 A | 5/2017 |
| WO | 2010/128659 A1 | 11/2010 |
| WO | 2017/006855 A1 | 1/2017 |
| WO | 2017/170348 A1 | 10/2017 |

OTHER PUBLICATIONS

Wikipedia: Sugar Substitute, pp. 1-14 (retrieved Oct. 2022) (XP055973324).
"Gilteritinib for the Treatment of FMS-like Tyrosine kinase 3 (FLT3) Mutation Positive Acute Myeloid Leukemia (AML)," Oncologic Drugs Advisory Committee, Pediatric Subcommittee Briefing Document, pp. 1-36 (2017) (XP055973430).
Gerad K. Bolhuis et al., "Polyols as Filler-Binders for Disintegrating Tablets Prepared by Direct Compaction," 35(6) Drug Dev. Ind. Pharm. 671-677 (Jun. 2009) (XP008162413).
Extended European Search Report in European Application No. 20784888.8 (Nov. 2022).
English Language Translation of Written Opinion in International Application No. PCT/JP2020/015225 (Jun. 2020).
Office Action in Canadian Application No. 3,131,461 (Dec. 2023).
Office Action in Vietnamese Application No. 1-2021-06491 (Feb. 2024).
International Report on Patentability in International Application No. PCT/JP2020/015225 with English Translation of Written Opinion (Sep. 2021).
Office Action in Canadian Application No. 3,131,461 (Jun. 2023).
International Preliminary Report on Patentability in International Application No. PCT/JP2020/015225 (Sep. 2021).

(Continued)

*Primary Examiner* — Golam M Shameem
(74) *Attorney, Agent, or Firm* — Venable LLP

(57) ABSTRACT

Provided is a pharmaceutical composition containing 6-ethyl-3-{3-methoxy-4-[4-(4-methylpiperazin-1-yl)piperidin-1-yl]anilino}-5-[(oxan-4-yl)amino]pyrazine-2-carboxamide or a pharmaceutically acceptable salt thereof and a sweetener for reducing the bitterness of gilteritinib, suppressing the decrease in dissolution stability of gilteritinib due to, for example, stress such as heat and/or humidity over time, and having excellent dissolution stability. The pharmaceutical composition contains gilteritinib or a pharmaceutically acceptable salt thereof, a sweetener, and sugars and/or sugar alcohols.

15 Claims, No Drawings

(56) References Cited

OTHER PUBLICATIONS

V.G. Belikov, "Pharmaceutical Chemistry," Part I, pp. 27-29 (2007).
A.I. Tentsova et al., "Modern Biopharmaceutical Aspects of Excipients," 7 Pharmacia 3-6 (2012).
Office Action in Russian Application No. 2021131991 (Jul. 2023).
First Office Action in Chinese Application No. 202080026179.1 (Oct. 2022).
Office Action in Russian Application No. 2021131991 (Feb. 2024).
T.G. Khoruzhaya et al., "Biopharmacy—Scientific Direction in the Development and Improvement of Drugs," pp. 1-75 (2006).
S.B. Setkina et al., "Biopharmaceutical Aspects of Drug Technology and Ways to Modify Bioavailability," 13(4) Vestnik VSMU 162-172 (2014).
Office Action in Taiwanese Application No. 109111460 (Aug. 2023).
Notice of the Result of Substantive Examination in Indonesian Application No. P00202109374 (Apr. 2023).
Second Office Action in Chinese Application No. 202080026179.1 (Apr. 2023).
XOSPATA Tablets 40 mg Package Insert (Nov. 2020).
Seiji Takae et al., "Pharmaceutical Companies' Efforts for Pediatric Products," 75 Pharmacology, Japanese Society of Pharmaceutical Sciences 32-37 (2015).
Written Opinion in Singapore Application No. 11202110315S (Jun. 2023).

PHARMACEUTICAL COMPOSITION

TECHNICAL FIELD

The present invention relates to a pharmaceutical composition comprising 6-ethyl-3-{3-methoxy-4-[4-(4-methylpiperazin-1-yl)piperidin-1-yl]anilino}-5-[(oxan-4-yl)amino]pyrazine-2-carboxamide or a pharmaceutically acceptable salt thereof.

BACKGROUND ART

6-Ethyl-3-{3-methoxy-4-[4-(4-methylpiperazin-1-yl)piperidin-1-yl]anilino}-5-[(oxan-4-yl)amino]pyrazine-2-carboxamide, or 6-ethyl-3-({3-methoxy-4-[4-(4-methoxypiperazin-1-yl)piperidin-1-yl]phenyl}amino)-5-(tetrahydro-2H-pyran-4-ylamino)pyrazine-2-carboxamide (hereinafter sometimes referred to as the International Nonproprietary Name (INN) gilteritinib) is a compound represented by the chemical structural formula of formula (I). It has been reported that gilteritinib or a pharmaceutically acceptable salt thereof has, for example, an inhibitory activity of a kinase activity of an EML4 (Echinoderm microtubule associated protein like-4)-ALK (Anaplastic lymphoma kinase) fusion protein, and is useful as an active ingredient of a pharmaceutical composition for treating cancer (Patent literature 1: WO2010/128659, Patent literature 2: WO2017/006855). Furthermore, for example, XOSPATA (registered trademark) Tablets 40 mg containing 40 mg of gilteritinib fumarate in terms of gilteritinib has been put on the market as a therapeutic agent for acute myeloid leukemia (Non-patent literature 1: XOSPATA Tablets 40 mg Package Insert (Japan), or PMDA, FDA, or EMA website). In this connection, gilteritinib fumarate is a generic name for a salt compound composed of the ratio of two molecules of gilteritinib to one molecule of fumaric acid, and is also referred to herein as gilteritinib hemifumarate.

[Chem. 1]

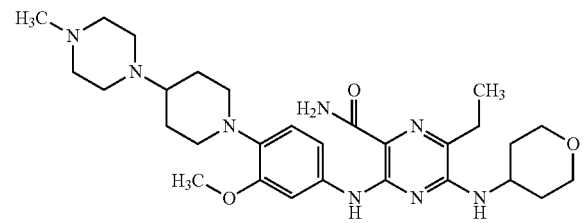

Formula (I)

In order to achieve drug treatment for cancer, it is necessary to formulate it to exhibit appropriate performance, and it is important to make it a formulation with good patient compliance. If the patient is an infant or child, there are many things to consider, such as dosage form, weight, taste, pharmaceutical additives, and the like. The dosage forms desired by infants and children are often liquids, powders, granules, syrups, and the like from the viewpoint of ease of swallowing. However, it is difficult to choose a liquid or syrup because many drugs are unstable in aqueous solution. Furthermore, it also takes time to weigh properly to take the correct amount. In the case of powders or granules, when they are packaged in a separate packaging sheet, since the drug is taken out by tearing the bag, there are problems that it is difficult for children to open, or that it is not possible to take an appropriate amount due to some spills. Additionally, in the case of drugs with strong bitterness, it is necessary to study techniques or pharmaceutical additives to reduce bitterness in the development of liquids, powders, or granules.

In recent years, as a dosage form that has been attracting attention, there are small tablets with a diameter of approximately 1 to 4 mm (hereinafter, sometimes referred to as mini-tablets or simply referred to as tablets). There is a report that mini-tablets can be taken even by children of age who cannot swallow normal-sized tablets (Non-patent literature 2: Takae et al., Pharmacology, Japanese Society of Pharmaceutical Sciences, 2015, vol. 75, p. 32-37). In addition, since the amount of active ingredient per tablet is smaller than that of normal size tablets, the dose adjustment required for pediatric preparations can be easily changed by the number of tablets.

Considering patients who cannot swallow even small tablets, there is a method of dissolving, dispersing, or suspending the required dose of tablets in a small amount of suitable solvent. However, for example, when tablets are suspended in a small amount of water, the drug dissolves and the effect of reducing bitterness is lost, and therefore, there is room for further improvement.

CITATION LIST

Patent Literature

[Patent literature 1] WO2010/128659
[Patent literature 2] WO2017/006855

Non-Patent Literature

[Non-patent literature 1] XOSPATA Tablets 40 mg Package Insert (Japan), or PMDA, FDA, or EMA website
[Non-patent literature 2] TAKAE, Seiji et al., Pharmacology, Japanese Society of Pharmaceutical Sciences, 2015, vol. 75, p. 32-37

SUMMARY OF INVENTION

Technical Problem

An object of the present invention is to provide a pharmaceutical composition containing gilteritinib or a pharmaceutically acceptable salt thereof, a sweetener for reducing bitterness, and an additive for imparting binding ability, and having excellent dissolution stability. In detail, an object of the present invention is to provide a pharmaceutical composition containing gilteritinib or a pharmaceutically acceptable salt thereof, a sweetener for reducing bitterness, and an additive for imparting binding ability, suppressing the decrease in dissolution stability of gilteritinib due to stress such as heat and/or humidity over time, and having excellent dissolution stability.

Solution to Problem

In order to reduce the bitterness observed when a pharmaceutical composition containing gilteritinib or a pharmaceutically acceptable salt thereof is suspended in a small amount of water, the present inventors conducted intensive studies on pharmaceutical additives for reducing the bitterness of gilteritinib or its pharmaceutically acceptable salt, and as a result, found sweeteners that reduce the specific bitterness. Additionally, the present inventors focused on the dissolution stability of gilteritinib and conducted intensive studies, and as a result, found that a pharmaceutical composition containing gilteritinib or a pharmaceutically acceptable salt thereof and having excellent dissolution stability could be provided by using additives for imparting the specific binding ability, and completed the present invention.

The present invention relates to the following:

[1] A pharmaceutical composition comprising 6-ethyl-3-{3-methoxy-4-[4-(4-methylpiperazin-1-yl)piperidin-1-yl]anilino}-5-[(oxan-4-yl)amino]pyrazine-2-carboxamide or a pharmaceutically acceptable salt thereof, a sweetener, and two or more sugars and/or sugar alcohols.

[2] The pharmaceutical composition of [1], wherein the sweetener is one, or two or more compounds selected from the group consisting of saccharin, acesulfame potassium, aspartame, and sucralose, and a mixture thereof.

[3] The pharmaceutical composition of [1] and [2], wherein the sweetener is sucralose.

[4] The pharmaceutical composition of any one of [1] to [3], wherein the sugars are disaccharides and the sugar alcohols have 6 or 12 carbon atoms.

[5] The pharmaceutical composition of any one of [1] to [4], wherein the two or more sugars and/or sugar alcohols are selected from the group consisting of mannitol, isomalt hydrate, maltitol, sorbitol, lactose, sucrose, and trehalose, and a mixture thereof.

[6] The pharmaceutical composition of any one of [1] to [5], wherein one of the two or more sugars and/or sugar alcohols is mannitol.

[7] The pharmaceutical composition of any one of [1] to [5], wherein one of the two or more sugars and/or sugar alcohols is selected from the group consisting of isomalt hydrate, maltitol, sorbitol, sucrose, and trehalose.

[8] The pharmaceutical composition of any one of [1] to [5], wherein one of the two or more sugars and/or sugar alcohols is isomalt hydrate.

[9] The pharmaceutical composition of [7] or [8], wherein a content of the isomalt hydrate, maltitol, sorbitol, sucrose, or trehalose described in [7] or [8] with respect to a weight of the pharmaceutical composition is 1% by weight to 20% by weight.

[10] The pharmaceutical composition of [7] or [8], wherein the isomalt hydrate, maltitol, sorbitol, sucrose, or trehalose described in [7] or [8] is used as a binder.

[11] The pharmaceutical composition of any one of [1] to [10], wherein the pharmaceutically acceptable salt thereof is a hemifumarate.

[12] The pharmaceutical composition of any one of [1] to [11], wherein the pharmaceutical composition is solid.

[13] The pharmaceutical composition of any one of [1] to [12], further comprising a disintegrating agent.

[14] The pharmaceutical composition of [12] or [13], wherein the pharmaceutical composition is a tablet.

[15] The pharmaceutical composition of any one of [1] to [14], wherein, after storing the pharmaceutical composition of any one of [1] to [14] at 40° C. and 75% relative humidity for 1 month, a dissolution rate of 6-ethyl-3-{3-methoxy-4-[4-(4-methylpiperazin-1-yl)piperidin-1-yl]anilino}-5-[(oxan-4-yl)amino]pyrazine-2-carboxamide after 15 minutes from the beginning of a Dissolution Test, a paddle method using 900 mL of 0.1 mol/L hydrochloric acid described in the Japanese Pharmacopoeia, Seventeenth Edition is 85% or more; or wherein, after storing the pharmaceutical composition of any one of [1] to [14] at 40° C. and 75% relative humidity for 2 months and/or 3 months, a dissolution rate of 6-ethyl-3-{3-methoxy-4-[4-(4-methylpiperazin-1-yl)piperidin-1-yl]anilino}-5-[(oxan-4-yl)amino]pyrazine-2-carboxamide after 15 minutes from the beginning of a Dissolution Test, a paddle method using 900 mL of 0.1 mol/L hydrochloric acid described in the Japanese Pharmacopoeia, Seventeenth Edition is 80% or more.

[16] The pharmaceutical composition of any one of [1] to [15], wherein the pharmaceutical composition is dissolved or dispersed in a suitable solvent, and is a solution, suspension, paste, or gel.

[17] A pharmaceutical composition comprising 6-ethyl-3-{3-methoxy-4-[4-(4-methylpiperazin-1-yl)piperidin-1-yl]anilino}-5-[(oxan-4-yl)amino]pyrazine-2-carboxamide hemifumarate, mannitol, sucralose, and isomalt hydrate.

[18] The pharmaceutical composition of any one of [1] to [17] produced by a production method comprising:
(1) preparing a binder liquid by dispersing or dissolving at least one sugars and/or sugar alcohols in a solvent;
(2) obtaining a mixture by mixing 6-ethyl-3-{3-methoxy-4-[4-(4-methylpiperazin-1-yl)piperidin-1-yl]anilino}-5-[(oxan-4-yl)amino]pyrazine-2-carboxamide or a pharmaceutically acceptable salt thereof, a sweetener, and at least one sugars and/or sugar alcohols; and
(3) spraying or adding the binder liquid obtained in step (1) to the mixture obtained in step (2) to form granules.

[19] A method of producing a pharmaceutical composition comprising 6-ethyl-3-{3-methoxy-4-[4-(4-methylpiperazin-1-yl)piperidin-1-yl]anilino}-5-[(oxan-4-yl)amino]pyrazine-2-carboxamide or a pharmaceutically acceptable salt thereof, and two or more sugars and/or sugar alcohols, said method comprising:
(1) preparing a binder liquid by dispersing or dissolving at least one sugars and/or sugar alcohols in a solvent;
(2) obtaining a mixture by mixing 6-ethyl-3-{3-methoxy-4-[4-(4-methylpiperazin-1-yl)piperidin-1-yl]anilino}-5-[(oxan-4-yl)amino]pyrazine-2-carboxamide or a pharmaceutically acceptable salt thereof, a sweetener, and at least one sugars and/or sugar alcohols; and
(3) spraying or adding the binder liquid obtained in step (1) to the mixture obtained in step (2) to form granules.

Advantageous Effects of Invention

According to the present invention, a pharmaceutical composition comprising gilteritinib or a pharmaceutically acceptable salt thereof, a sweetener that reduces bitterness, and two or more sugars and/or sugar alcohols, and having excellent dissolution stability, in detail, a pharmaceutical composition suppressing the decrease in dissolution properties of gilteritinib due to stress such as heat and/or humidity, and having excellent dissolution stability can be provided.

According to the present invention, a liquid pharmaceutical composition, such as a solution, suspension, paste, or gel, prepared by dissolving or dispersing a pharmaceutical composition comprising gilteritinib or a pharmaceutically acceptable salt thereof, a sweetener that reduces bitterness, and two or more sugars and/or sugar alcohols in a suitable solvent can be provided.

According to the present invention, a pharmaceutical composition comprising gilteritinib or a pharmaceutically acceptable salt thereof, a sweetener that reduces bitterness, and two or more sugars and/or sugar alcohols, in detail, a pharmaceutical composition suppressing the decrease in dissolution properties of gilteritinib due to stress such as heat and/or humidity, and having excellent dissolution stability, can be provided by a method comprising the step of preparing a binder liquid by dispersing or dissolving at least one sugars and/or sugar alcohols in a solvent; the step of obtaining a mixture by mixing gilteritinib or a pharmaceutically acceptable salt thereof, a sweetener that reduces bitterness, and at least one sugars and/or sugar alcohols; and the step of spraying or adding the binder liquid obtained in the above step to the mixture obtained in the above step to form granules.

According to the present invention, a pharmaceutical composition comprising gilteritinib or a pharmaceutically acceptable salt thereof, mannitol, sucralose, and isomalt hydrate, in detail, a pharmaceutical composition suppressing the decrease in dissolution properties of gilteritinib due to stress such as heat and/or humidity, and having excellent dissolution stability can be provided.

According to the present invention, a method of producing a pharmaceutical composition comprising gilteritinib or a pharmaceutically acceptable salt thereof, a sweetener, and two or more sugars and/or sugar alcohols, in detail, a method comprising the step of preparing a binder liquid by dispersing or dissolving at least one sugars and/or sugar alcohols in a solvent; the step of obtaining a mixture by mixing gilteritinib or a pharmaceutically acceptable salt thereof, a sweetener that reduces bitterness, and at least one sugars and/or sugar alcohols; and the step of spraying or adding the binder liquid obtained in the above step to the mixture obtained in the above step to form granules can be provided.

DESCRIPTION OF EMBODIMENTS

The present invention relates to a pharmaceutical composition comprising gilteritinib or a pharmaceutically acceptable salt thereof, a sweetener, and two or more sugars and/or sugar alcohols. Furthermore, the present invention relates to a pharmaceutical composition comprising gilteritinib hemifumarate, mannitol, sucralose, and isomalt hydrate.

The term "sweetener" as used herein is an additive for sweetening a pharmaceutical composition. Examples of the sweetener include saccharin or sodium saccharin, glycyrrhizinic acid, aspartame, *stevia*, thaumatin, acesulfame potassium, sodium cyclamate, advantame, steviol glycosides, neohesperidin dihydrochalcone, neotheme, taumatin, other sweet proteins, saponins such as osladine or gicillidine, sucralose, a mixture thereof, and the like. The "to reduce bitterness" as used herein means to suppress the bitterness to the extent that gilteritinib or a pharmaceutically acceptable salt thereof that has a strong bitterness by nature can be taken. A sweetener preferable for reducing the bitterness observed when gilteritinib or a pharmaceutically acceptable salt thereof is suspended or the like in a small amount of water or the like is saccharin, acesulfame potassium, aspartame, sucralose, or a mixture thereof, more preferably aspartame or sucralose, still more preferably sucralose.

The "saccharin" as used herein is also known as o-sulfobenzimide, o-sulfimide benzoate, or 2-sulfobenzoate imide, and is a sweetener usually used as a water-soluble sodium salt (sodium saccharinate).

The "acesulfame potassium" as used herein is an artificial sweetener.

The "aspartame" as used herein is a sweetener having a structure in which the amino group of a phenylalanine methyl ester formed by dehydration condensation of L-phenylalanine and methanol, and the carboxy group of L-aspartic acid are dehydrated and condensed to form a peptide bond.

The "sucralose" as used herein is the registered trademark name of 4,1',6'-trichlorogalactosucrose, and its chemical name is 1,6-dichloro-1,6-dideoxy-β-D-fructofuranosyl-4-chloro-4-deoxy-α-D-garactopyranoside, and is a sweetener obtained by selectively replacing three hydroxyl groups of sucrose with chlorine atoms.

The proportion of a sweetener required to reduce the bitterness observed when gilteritinib or a pharmaceutically acceptable salt thereof is suspended or the like in a small amount of a solvent such as water or the like can be determined by, for example, an in vitro method using a device generally called a taste sensor, or an in vivo method such as a sensory test or the like using a test panel. Examples of an evaluation method of the sensory test include a method in which after a test solution containing an appropriate amount of a sweetener in a solution in which Compound A or a substance having a bitterness similar to that of Compound A or a pharmaceutically acceptable salt thereof is dissolved at a concentration of 10 mg/mL is put in the mouth and immediately spit out, the bitterness is scored immediately after spitting out to 30 minutes after spitting out, but are not limited thereto. The appropriate content of the sweetener differs depending on the type of sweetener, but with respect to the weight of the pharmaceutical composition, it is typically 0.001 to 70.0% by weight, preferably 0.01 to 60.0% by weight, more preferably 0.1 to 50.0% by weight, still more preferably 1.0 to 40.0% by weight, still more preferably 5.0 to 35.0% by weight, still more preferably 5.5 to 33.3% by weight, still more preferably 10.0 to 30.0% by weight, still more preferably 15.0 to 30.0% by weight, and still more preferably 20.0 to 25.0% by weight. Each lower limit and each upper limit can be arbitrarily combined as desired.

The pharmaceutical composition of the present invention contains two or more kinds of sugars and/or sugar alcohols. Therefore, the pharmaceutical composition contains at least two sugars, at least one sugar and at least one sugar alcohol, or at least two sugar alcohols.

Examples of the "sugars" include monosaccharides such as glucose, galactose, and the like, and disaccharides such as sucrose, lactose, trehalose, maltose, and the like, but are not limited thereto.

The term "sugar alcohols" is a type of sugar produced by reducing a carbonyl group of aldose or ketose. Sugar alcohols are a mixture of compounds produced by hydrogenation of sugars and having the general formula $HOCH_2(CHOH)_nCH_2OH$, such as mannitol, xylitol, sorbitol, inositol, maltitol, lactitol, and the like. Examples in which n is 4 or 10, i.e., examples having 6 or 12 carbon atoms, include mannitol, isomalt hydrate, maltitol, sorbitol, and the like, but are not limited thereto.

In the "sugars and/or sugar alcohols" as used in the present invention, the sugars may be selected from, preferably lactose, sucrose, trehalose, maltose, glucose, or fructose, and more preferably lactose, sucrose, or trehalose. The sugar alcohols may be selected from, preferably mannitol, isomalt hydrate, maltitol, sorbitol, xylitol, lactitol, or erythritol, more preferably mannitol, isomalt hydrate, maltitol, or sorbitol, and still more preferably mannitol or isomalt hydrate. The sugars and/or sugar alcohols may be selected from, preferably lactose, mannitol, isomalt hydrate, maltitol, sorbitol, sucrose, or trehalose, more preferably mannitol, isomalt hydrate, maltitol, or sorbitol, still more preferably mannitol, isomalt hydrate, or sorbitol, and still more preferably mannitol or isomalt hydrate.

As a more preferred embodiment, one of the two or more sugars and/or sugar alcohols contained in the pharmaceutical composition of the present invention is mannitol, and may be used, for example, as a filler. In the pharmaceutical composition in which one of the two or more sugars and/or sugar alcohols contained in the pharmaceutical composition of the present invention is mannitol, one sugar and/or sugar alcohol among the remaining at least one sugar and/or sugar alcohol may be used, for example, as an additive for imparting binding ability. It may be selected from, preferably isomalt hydrate, maltitol, sorbitol, sucrose, or trehalose, more preferably isomalt hydrate, maltitol, or sorbitol, and still more preferably isomalt hydrate or sorbitol.

As a still more preferred embodiment, two or more sugars and/or sugar alcohols contained in the pharmaceutical composition of the present invention are mannitol and isomalt hydrate. Isomalt hydrate is a mixture of 6-0-α-D-glucopyranosyl-D-sorbitol and 1-0-α-D-glucopyranosyl-D-mannitol, but it is not limited to the hydrated form.

The content of two or more sugars and/or sugar alcohols contained in the pharmaceutical composition of the present invention is, with respect to the weight of the pharmaceutical composition, typically 1 to 90% by weight, preferably 5 to 70% by weight, more preferably 10 to 60% by weight, still more preferably 15 to 50% by weight, still more preferably 25 to 45% by weight, still more preferably 30 to 45% by weight, still more preferably 35 to 42% by weight, and still more preferably 36 to 42% by weight.

In the pharmaceutical composition in which one of the two or more sugars and/or sugar alcohols contained in the pharmaceutical composition of the present invention is mannitol, the content of one sugar and/or sugar alcohol among the remaining at least one sugar and/or sugar alcohol, with respect to the weight of the pharmaceutical composition, typically 1 to 20% by weight, preferably 3 to 15% by weight, more preferably 5 to 15% by weight, still more preferably 7 to 12%, and still more preferably 9 to 11% by weight. The content of mannitol in the pharmaceutical composition of the present invention containing mannitol, with respect to the weight of the pharmaceutical composition, typically 1 to 40% by weight, preferably 10 to 40% by weight, more preferably 20 to 40% by weight, still more preferably 25 to 35% by weight, and still more preferably 27 to 33% by weight.

Each lower limit and each upper limit can be arbitrarily combined as desired.

The term "dissolution stability" as used herein means dissolution properties of gilteritinib after a certain period of exposure to heat and/or humidity. The wording "excellent in dissolution stability" or "to suppress the decrease in dissolution stability over time" as used herein means that, after storing a pharmaceutical composition (for example, tablets as a dosage form) typically at 70° C. for 9 days, preferably at 40° C. and 75% relative humidity (hereinafter X % relative humidity is sometimes abbreviated as X % RH) for 1 month, 2 months, 3 months, or 6 months, a dissolution rate of gilteritinib after 15 minutes or 30 minutes from the beginning of a Dissolution Test, a paddle method using 900 mL of 0.1 mol/L hydrochloric acid at a paddle rotation speed of 50 rpm, as described in the Japanese Pharmacopoeia, Seventeenth Edition, is high. The fact that the dissolution rate of gilteritinib after 15 minutes from the beginning of the Dissolution Test is high means typically 80% or more, preferably 85% or more. In another embodiment, it means that the dissolution rate of gilteritinib after 30 minutes from the beginning of the Dissolution Test is typically 90% or more. In another embodiment, it means that, after storing a pharmaceutical composition at 40° C. and 75% relative humidity for 1 month, 85% or more gilteritinib is dissolved after 15 minutes from the beginning of a Dissolution Test, a paddle method using 900 mL of 0.1 mol/L hydrochloric acid described in the Japanese Pharmacopoeia, Seventeenth Edition, or that, after storing a pharmaceutical composition at 40° C. and 75% relative humidity for 2 months and/or 3 months, 80% or more gilteritinib is dissolved after 15 minutes from the beginning of a Dissolution Test, a paddle method using 900 mL of 0.1 mol/L hydrochloric acid described in the Japanese Pharmacopoeia, Seventeenth Edition.

Gilteritinib or a pharmaceutically acceptable salt thereof used in the present invention can be easily obtained, for example, by a method described in Patent literature 1 (WO 2010/128659), or in a similar fashion to that.

Gilteritinib may be in a free form, which does not form a salt, and may form a pharmaceutically acceptable salt with an acid. Examples of such a salt include an acid addition salt with an inorganic acid, such as hydrochloride, hydrobromide, hydroiodide, sulfate, nitrate, phosphate, or the like; and an acid addition salt with an organic acid, such as formate, acetate, propionate, oxalate, malonate, succinate, fumarate, hemifumarate, maleate, lactate, malate, citrate, tartrate, carbonate, picrate, methanesulfonate, ethanesulfonate, glutamate, or the like. These salts can be prepared by conventional methods. Hemifumarate is preferable.

The proportion of crystals of gilteritinib or a pharmaceutically acceptable salt thereof, which are used in the present invention, is not particularly limited, so long as it is within a range where it is stable during storage. When the pharmaceutical composition is solid, the proportion of the crystals can be calculated by, for example, a differential scanning calorimeter analysis (DSC analysis) method, a powder X-ray diffraction method, a solid-state NMR method, a near-infrared spectroscopy (NIR) method, or the like. For example, as a method of calculating the proportion of crystals of gilteritinib hemifumarate in gilteritinib hemifumarate, for example, the spectrum is measured, as a near-infrared spectroscopy measurement, by a Fourier transform near-infrared spectrometer (MPA, Bruker Optics) (measurement range; 12500 cm$^{-1}$ to 5800 cm$^{-1}$, resolution; 8 cm$^{-1}$, number of scans; 32), and the obtained spectrum is secondary-differentiated (Savitzky-Golay convolution method), and can be analyzed using a near-infrared spectrum analysis software (for example, OPUS, Bruker Optics). The pharmaceutical composition is powdered using a mortar and pestle to measure the spectrum. Before the spectrum measurement of the pharmaceutical composition, spectra of preparations, in which crystals of gilteritinib hemifumarate are mixed in various proportions, are regression-analyzed by a partial least square method to create a calibration curve, and each spectrum obtained from the pharmaceutical composition is interpolated into the calibration curve to calculate the proportion of crystals of gilteritinib hemifumarate.

The proportion of the crystals is, for example, with respect to the total amount of gilteritinib or a pharmaceutically acceptable salt thereof, typically 60% or more, preferably 60% to 100%, more preferably 70% to 100%, still more preferably 80% to 100%, and still more preferably 90% to 100%. Furthermore, the proportion of the crystals is, for example, with respect to the total amount of gilteritinib or a pharmaceutically acceptable salt thereof, preferably 60% to less than 100%, more preferably 70% to less than 100%, still more preferably 80% to less than 100%, and still more preferably 90% to less than 100%. In connection with this, numerical values used are interpreted as a larger variable value, in general, within an experimental error (for example, within the 95% confidence interval for the mean), or within ±10% of the indicated value, and all the values of the variable.

The dose of gilteritinib or a pharmaceutically acceptable salt thereof can be appropriately determined depending on individual cases taken into consideration symptoms, age, sex, or the like of the patient. The daily dosage for an adult is typically 5 to 300 mg, preferably 10 to 200 mg, more preferably 20 to 180 mg, still more preferably 40 to 160 mg, still more preferably 80 to 140 mg, and still more preferably 110 to 130 mg, as gilteritinib. This is administered in one dose, or divided into two to four doses per day. Each lower limit and each upper limit can be arbitrarily combined as desired.

The content of gilteritinib or a pharmaceutically acceptable salt thereof is, for example, with respect to the weight of the pharmaceutical composition, 1 to 90% by weight, preferably 5 to 50% by weight, more preferably 10 to 40% by weight, and still more preferably 25 to 35% by weight. The amount contained of gilteritinib or a pharmaceutically acceptable salt thereof is, in the whole formulation, 5 to 300 mg, preferably 10 to 200 mg, more preferably 10 to 50 mg, and still more preferably 10 to 40 mg. Each lower limit and each upper limit can be arbitrarily combined as desired.

The pharmaceutical composition of the present invention may be various preparations, such as tablets, capsules, powders, granules, fine granules, dry syrups, or the like, but is not limited thereto. The tablets include an uncoated tablet without film coating, a film coated tablet with film coating, an orally disintegrating tablet, a dissolving tablet, and a mini tablet, but are not limited thereto. Tablets or capsules are preferable, and tablets are more preferable.

The liquid preparation of the present invention includes a solution, a suspension, a syrup, or the like, but is not limited thereto. The liquid preparation of the present invention can be prepared by dissolving, dispersing, suspending a pharmaceutical composition containing gilteritinib or a pharmaceutically acceptable salt thereof, a sweetener, and two or more sugars/sugar alcohols in a solvent. Examples of the solvent include water, juice, milk, or the like, but are not limited thereto.

The weight of the pharmaceutical composition of the present invention is not particularly limited, so long as the patient can take it. The weight of the pharmaceutical composition is typically 5 to 600 mg, preferably 270 to 600 mg, more preferably 10 to 500 mg, still more preferably 15 to 300 mg, still more preferably 30 to 270 mg, still more preferably 35 to 180 mg, still more preferably 100 to 140 mg, and still more preferably 30 to 50 mg. Each lower limit and each upper limit can be arbitrarily combined as desired.

In the pharmaceutical composition of the present invention, various pharmaceutical additives, such as binders, corrigents, effervescent agents, flavors, buffers, antioxidants, surfactants, suspensions, film coating agents, disintegrating agents, lubricants, and the like, may be appropriately used, if desired, to the extent that the effects of the present invention can be achieved. In the present invention, these pharmaceutical additives may be appropriately added alone, or as a combination of two or more, in appropriate amounts.

The "binder" used in the present invention means an agent used to act between particles and maintain them as an aggregate. Examples of the binder include sugars, sugar alcohols, cellulose derivatives such as hydroxypropyl cellulose (HPC), and soluble polymers, but are not limited thereto. Preferably, the sugars and/or sugar alcohols contained in the pharmaceutical composition of the present invention can function as the binder. In this connection, an additional binder can be added in the present invention, if desired, to the extent that the effects of the present invention can be achieved, but the pharmaceutical composition of the present invention does not substantially contain HPC.

Examples of the corrigents include citric acid, tartaric acid, malic acid, and the like, but are not limited thereto.

Examples of the effervescent agents include sodium bicarbonate, and the like, but are not limited thereto.

Examples of the flavors include lemon, orange, cherry, raspberry, menthol, and the like, but are not limited thereto.

Examples of the buffers include citric acid, succinic acid, fumaric acid, tartaric acid, ascorbic acid, and salts thereof; glutamic acid, glutamine, glycine, aspartic acid, alanine, arginine, and salts thereof; magnesium oxide, zinc oxide, magnesium hydroxide, phosphoric acid, boric acid, and salts thereof; and the like, but are not limited thereto.

Examples of the antioxidants include citric acid, sodium nitrite, ascorbic acid, sodium edetate, soybean lecithin, natural vitamin E, sodium pyrosulfite, dibutylhydroxytoluene, and the like, but are not limited thereto.

Examples of the surfactants include polysorbate 80, sodium lauryl sulfate, polyoxyethylene hydrogenated castor oil, and the like, but are not limited thereto.

Examples of the suspensions include crystalline cellulose, sodium carmellose, xanthan gum, agar, and the like, but are not limited thereto.

The pharmaceutical composition of the present invention can further contain a film coating agent. The film coating agent is not particularly limited, so long as a pharmaceutical composition having excellent dissolution stability can be provided. Examples of the film coating agent include pharmaceutically acceptable polymers, such as polyvinyl alcohol, hydroxypropyl methylcellulose (HPMC), hydroxypropyl cellulose, ethyl cellulose (EC), polyvinyl alcohol (PVA), polyvinyl alcohol-polyethylene glycol graft copolymers, and the like; pharmaceutically acceptable plasticizers, such as propylene glycol, polyethylene glycol (PEG), glycerol, triacetin (glycerin triacetic acid), triethyl citrate (TEC), and the like; oils, such as mineral oil, vegetable oil, and the like; pharmaceutically acceptable lubricants or brighteners, such as talc, wax, carnauba wax, and the like; pharmaceutically acceptable colorants, such as titanium oxide, iron sesquioxide, and the like; sweeteners: flavors, such as mint, berry, vanilla, and the like; viscosity modifiers, such as polydextrose, starch, acacia, xanthan gum, and the like; and the like, but are not limited thereto. As the film coating agent, a commercially available rapid-release coating agent, such as Opadry (registered trademark) (manufactured by Colorcon Japan) containing PVA, HPMC, or polyvinyl alcohol-polyethylene glycol graft copolymers as the polymer, PEG as the plasticizer, talc as the lubricant, and iron sesquioxide as the colorant, is preferable; and a commercially available rapid-release coating agent, such as Opadry (registered trademark) (manufactured by Colorcon Japan) containing HPMC as the polymer, PEG as the plasticizer, talc as the lubricant, and iron sesquioxide as the colorant, is more preferable.

The pharmaceutical composition of the present invention further contains a disintegrating agent. The disintegrating agent is not particularly limited so long as it can provide a pharmaceutical composition having excellent dissolution stability. Examples of the disintegrating agent include carmellose, carmellose calcium, croscarmellose sodium, low-substituted hydroxypropyl cellulose, corn starch, potato starch, rice starch, partially pregelatinized starch, pregelatinized starch, and crospovidone, but are not limited thereto. Low-substituted hydroxypropyl cellulose is preferable. The disintegrating agent can be part of a disintegrating agent-filler mixture, for example, mannitol/starch is 8:2 (PEARLITOL FLASH manufactured by Roquette). The disintegrating agent contained in the pharmaceutical composition used in the present invention can be added alone, or as a combination of two or more.

The content of the disintegrating agent used in the present invention is, with respect to the weight of the pharmaceutical composition, typically 1 to 20% by weight, preferably 2 to 15% by weight, more preferably 3 to 10% by weight, and still more preferably 4 to 6% by weight. Each lower limit and each upper limit can be arbitrarily combined as desired.

The pharmaceutical composition of the present invention can further contain the lubricant. The lubricant is not particularly limited, so long as during the formulation step (particularly the molding step), it is possible to suppress adhesion of the pharmaceutical composition, for example, to a mortar, pestle, or the like, and an excessive increase or the like in the force for removing the tablet from the mortar (hereinafter sometimes referred to as the push-up pressure) in a tableting device, and a pharmaceutical composition having excellent dissolution stability can be provided. Examples of the lubricant include magnesium stearate (hereinafter sometimes referred to as Mg-St), calcium stearate, sodium stearyl fumarate, and talc, but are not limited thereto. The lubricant contained in the pharmaceutical composition used in the present invention can be added alone, or as a combination of two or more.

The content of the lubricant used in the present invention is, with respect to the weight of the pharmaceutical composition, typically 0.5 to 5% by weight, preferably 1 to 3% by weight, and more preferably 1.5 to 2% by weight. Each lower limit and each upper limit can be arbitrarily combined as desired.

The present invention also relates to a method of producing a pharmaceutical composition comprising gilteritinib or a pharmaceutically acceptable salt thereof, and two or more sugars and/or sugar alcohols, said method comprising:
(1) preparing a binder liquid by dispersing or dissolving at least one sugars and/or sugar alcohols in a solvent;
(2) obtaining a mixture by mixing gilteritinib or a pharmaceutically acceptable salt thereof, a sweetener, and at least one sugars and/or sugar alcohols; and
(3) spraying or adding the binder liquid obtained in step (1) to the mixture obtained in step (2) to form granules.

The "binder" used in the present invention means an agent used to act between particles and maintain them as an aggregate. The "binder liquid" used in the present invention means a liquid obtained by dispersing or dissolving the binder in a solvent. Example of the solvent include water, acetone, methanol, and ethanol, but are not limited thereto.

With respect to the terms "sweetener", "sugars and/or sugar alcohols", or the like, which are used in the production method of the present invention, the explanations therefor described in the pharmaceutical composition of the present invention can be directly applied.

With respect to the content of each component, the blending method, or the like in the production method of the present invention, the explanations therefor described in the pharmaceutical composition of the present invention can be directly applied.

The method of producing a pharmaceutical composition of the present invention will be explained below, but includes a known method comprising, for example, pulverization, mixing, granulation, drying, sieving, sizing, molding (tableting), film coating, crystallization, and the like.

Pulverization Step and Mixing Step

In the pulverization step, both the apparatus and the means are not particularly limited, so long as it is a method in which gilteritinib or a pharmaceutically acceptable salt thereof and appropriate pharmaceutical additives can be pulverized in an ordinary pharmaceutical manner. Examples of a pulverizer include a hammer mill, a ball mill, a jet mill, a colloid mill, and the like, but are not limited thereto. The conditions for pulverization may be appropriately selected and are not particularly limited thereto.

In the step of mixing components subsequent to the pulverization step, both the apparatus and the means are not particularly limited, so long as it is a method in which the components can be uniformly mixed in an ordinary pharmaceutical manner.

Granulation Step

In the granulation step, both the apparatus and the means are not particularly limited, so long as it is a method in which gilteritinib or a pharmaceutically acceptable salt thereof and appropriate pharmaceutical additives can be granulated in an ordinary pharmaceutical manner.

Examples of a granulation method and a granulation apparatus, which are used in a wet granulation using a solvent such as water, or a binder liquid prepared by dispersing or dissolving an appropriate amount of binder in water or the like, include a high shear granulation method, a milling (pulverization) granulation method, a fluidized bed granulation method, an extrusion granulation method, a tumbling granulation method, and a spray granulation method; and apparatuses and the like, which are used in these methods, but are not limited thereto.

As a granulation method, for example, a mixture containing gilteritinib or a pharmaceutically acceptable salt thereof and a sweetener can be granulated by spraying or adding a binder liquid obtained by dispersing or dissolving isomalt hydrate in a solvent such as water to obtain a granulated product. As a method not using water during granulation, a wet granulation method using a non-aqueous solvent or a dry granulation method not using a solvent can be selected.

Drying Step

In the drying step, both the apparatus and the means are not particularly limited, so long as it is a method in which the granulated product can be dried in an ordinary pharmaceutical manner. Examples of the apparatus include a forced-air dryer, a dryer under reduced pressure, a vacuum dryer, a fluidized bed granulation dryer, and the like, but are not limited thereto.

Sieving and Sizing Step

In the sieving and sizing step, both the apparatus and the means are not particularly limited, so long as it is a method in which the dried product can be sieved or sized in an ordinary pharmaceutical manner. Examples of the apparatus include a sieve, a comil, a power mill, and the like, but are not limited thereto.

Molding (Tableting) Step

In the molding step, both the apparatus and the means are not particularly limited, so long as it is a method of molding the pharmaceutical composition of the present invention. Examples of the method include a method in which, without the granulation and drying step, gilteritinib or a pharmaceutically acceptable salt thereof and appropriate pharmaceutical additives are mixed, and directly compression-molded to prepare the pharmaceutical composition; a method in which gilteritinib or a pharmaceutically acceptable salt thereof and appropriate pharmaceutical additives are granulated and dried, and compression-molded to prepare the pharmaceutical composition; a method in which gilteritinib or a pharmaceutically acceptable salt thereof and appropriate pharmaceutical additives are granulated, and further mixed with a lubricant, and the mixture is compression-molded to prepare the pharmaceutical composition (for example, uncoated tablets); and the like, but are not limited thereto.

Examples of a tableting machine include a rotary tableting machine, an oil press, and the like. The conditions for tableting, such as tableting pressure, are not particularly limited, so long as it is tableting pressure capable of compression-molding. For example, the tableting pressure (main pressure) when compression-molding is carried out using a rotary tableting machine (EX-10, manufactured by HATA TEKKOSHO) may be 0.5 to 20.0 kN, preferably 1.0 to 10.0 kN, and more preferably 1.5 to 4.5 kN. Each lower limit and each upper limit can be arbitrarily combined as desired.

The hardness of the uncoated tablet is not particularly limited, so long as it is not damaged from the manufacturing process to the distribution process. For example, the hardness when the hardness of a tableted product is measured using a rotary tableting machine (HT-CVX-TYPEIII20, manufactured by HATA TEKKOSHO) is 30 N or more, preferably 42 N or more, more preferably 64 N or more, and still more preferably 80 N or more. The upper limit of hardness is 400 N or less. When, for example, a rotary tableting machine, an oil press, or the like is used as the tableting machine, since gilteritinib or a pharmaceutically acceptable salt thereof has strong metal-adhering properties, continuous tableting causes sticking to the pestle, difficulty in removing compression molded tablets from the mortar, and an increase in push-up pressure. Since when sticking occurs or the push-up pressure increases, not only does it affect the appearance of the tablets, but it also puts a burden on the mortar and pestle and the tableting machine, it should be improved. Examples of the improvement method include a rigid chrome treatment or chrome nitride treatment of the mortar and pestle, and the like, but are not limited thereto.

Film Coating Step

After tableting, the surface of the pharmaceutical composition (for example, uncoated tablets) may be film coated. The method of film coating is not particularly limited, so long as it may be coated in an ordinary pharmaceutical manner. Examples of the coating include pan coating, flow coating, dip coating, and the like, but are not limited thereto.

Crystallization Step

When the proportion of crystals of gilteritinib or a pharmaceutically acceptable salt thereof is reduced, a step of promoting crystallization may be adopted. Examples of the step include a microwave irradiation treatment, an ultrasonic irradiation treatment, a low frequency irradiation treatment, a thermal electron irradiation treatment, and the like, but are not limited thereto.

As the microwave irradiation treatment, for example, a wavelength of 10 MHz to 25 GHz may be irradiated, but it is not limited thereto. Although the treatment time depends on the degree of an initial crystal proportion, or pharmaceutical additive components, it may be performed, for example, for 10 seconds to 60 minutes. The irradiation may be continuous or intermittent, and at any time.

As the ultrasonic irradiation treatment, for example, sound waves with a frequency of 10 kHz to 600 kHz may be irradiated, but it is not limited thereto. Although the treatment time depends on the degree of a crystal proportion, or pharmaceutical additive components, it may be performed, for example, for 10 seconds to 24 hours. The irradiation may be continuous or intermittent, and at any time.

EXAMPLES

Gilteritinib hemifumarate, which was used in the Examples or the like, had been prepared in accordance with a method described in Patent literature 1 (WO 2010/128659), or in a similar fashion to that.

As compounds or agents described in the Examples or the like, PEARLITOL (registered trademark) 50C (manufactured by ROQUETTE), which was mannitol;

sucralose (registered trademark) (P) (manufactured by San-Ei Gen F.F.I.), which was sucralose;

Ajinomoto KK aspartame (manufactured by Ajinomoto), which was aspartame; HPC L (manufactured by Nippon Soda), which was hydroxypropyl cellulose (hereinafter sometimes referred to as HPC);

galenIQ 721 (manufactured by BENEO-PALATINIT), which was isomalt hydrate; Sweet Peral (registered trademark) P200 (manufactured by ROQUETTE), which was maltitol;

NEOSORB (registered trademark) XTAB 290 (manufactured by ROQUETTE), which was sorbitol;

sucrose (UE-E) (manufactured by KANTO CHEMICAL), which was sucrose;

trehalose (P) (manufactured by Asahi Kasei), which was trehalose;

L-HPC (registered trademark) LH-21 (manufactured by Shin-Etsu Chemical), which was low-substituted hydroxypropyl cellulose;

Parteck (registered trademark) LUB MST (manufactured by Merck KGaA), which was Mg-St;

Opadry (registered trademark) (manufactured by Colorcon Japan) or Opadry (registered trademark) QX (manufactured by Colorcon Japan), which were film coating agents: were used.

Experimental Example

To a solution prepared by dissolving gilteritinib hemifumarate in water at a concentration of 1.05 mg/mL, several kinds of sweeteners were added to prepare test solution. A sensory test of the prepared test solution revealed that, in particular, sucralose reduced the bitterness of gilteritinib hemifumarate.

<<Formulations of Referential Example, Comparative Example 1, Example 1, and Example 2>>

Table 1 shows the formulations of Referential Example that is a formulation not containing two or more sugars and/or sugar alcohols, Comparative Example 1 that is a formulation in which part of mannitol in Referential Example was replaced with sucralose as a sweetener, Example 1 in which HPC in Comparative Example 1 was replaced with isomalt hydrate, and Example 2 in which the composition ratio was slightly different from that of Example 1. "Referential Example" as used herein means an example not substantially containing a sweetener, "Example" means an example containing a sweetener and having excellent dissolution stability, and "Comparative Example" means an example containing a sweetener and having poor dissolution stability.

TABLE 1

| Component | Referential Example | Comparative Example 1 | Example 1 | Example 2 |
|---|---|---|---|---|
| Gilteritinib hemifumarate | 11.05 | 11.05 | 11.05 | 11.05 |
| Mannitol | 20.625 | 12.625 | 10.61 | 12.41 |
| Sucrose | — | 8.0 | 8.4 | 8.4 |
| HPC | 1.05 | 1.05 | — | — |
| Isomalt hydrate | — | — | 3.6 | 3.48 |
| L-HPC | 1.75 | 1.75 | 1.8 | 1.8 |
| Mg—St | 0.525 | 0.525 | 0.72 | 0.54 |
| Uncoated tablet | 35.0 | 35.0 | 36.18 | 37.68 |
| Opadry (registered trademark) | 1.05 | 1.05 | — | — |
| Opadry (registered trademark) QX | — | — | 1.08 | 1.13 |
| Film coated tablet | 36.05 | 36.05 | 37.26 | 38.81 |

Unit: mg

<<Preparation of Tablets of Referential Example>>

In accordance with the formulation described in Table 1, 2223.0 g of gilteritinib hemifumarate and 4112.0 g of mannitol were mixed using a fluidized bed granulator (GPCG-PRO-5, manufactured by Powrex), and the mixture was granulated by spraying 3008 g of an HPC aqueous solution (solid content: 7% by weight) as a binder, and dried to obtain a granulated product. After sieving to remove aggregates, 326.8 g of L-HPC and 98.05 g of Mg-St were added to the obtained granulated product, and mixed using a mixer (Container Mixer PM200 (60 L container), manufactured by HIROSHIMA METAL & MACHINERY) to obtain a mixed product. The obtained mixed product was formed into tablets using a rotary tableting machine (HT-CVX-TYPEIII20, manufactured by HATA TEKKOSHO) to obtain uncoated tablets. The obtained uncoated tablets (5158.8 g) were put into a film coating machine (PRC-20/60 (20 L container), manufactured by Powrex) and film coated with a liquid prepared by dispersing or dissolving Opadry (registered trademark) in purified water, to obtain film coated tablets of Referential Example.

<<Preparation of Tablets of Comparative Example 1>>

In accordance with the formulation described in Table 1, 165.8 g of gilteritinib hemifumarate, 189.4 g of mannitol, and 120.0 g of sucralose were mixed using a fluidized bed granulator (FLO-1, manufactured by Freund Corporation), and the mixture was granulated by spraying 225 g of an HPC aqueous solution (solid content: 7% by weight) as a binder, and dried to obtain a granulated product. After sieving to remove aggregates, 196.3 g was weighed from 473.4 g of the obtained granulated product, and 10.5 g of L-HPC and 3.15 g of Mg-St were added thereto and hand-mixed using a polyethylene bag to obtain a mixed product. The obtained mixed product was formed into tablets using a rotary tableting machine (EX-10, manufactured by HATA TEKKOSHO) to obtain uncoated tablets. The obtained uncoated tablets (35.0 g) were put into a film coating machine (Flow Coater mini, manufactured by Powrex) and film coated with a liquid prepared by dispersing or dissolving Opadry (registered trademark) in purified water, to obtain film coated tablets of Comparative Example 1.

<<Preparation of Tablets of Example 1>>

In accordance with the formulation described in Table 1, 2.21 kg of gilteritinib hemifumarate, 2122.0 g of mannitol, and 1680.0 g of sucralose were mixed using a fluidized bed granulator (GPCG-PRO-5, manufactured by Powrex), and the mixture was granulated by spraying 3602 g of an isomalt hydrate aqueous solution (solid content: 20% by weight) as a binder, and dried to obtain a granulated product. After sieving to remove aggregates, 5385.6 g was weighed from 6377.5 g of the obtained granulated product, and 288.0 g of L-HPC and 115.2 g of Mg-St were added thereto and mixed using a mixer (Container Mixer PM200 (60 L container), manufactured by HIROSHIMA METAL & MACHINERY) to obtain a mixed product. The obtained mixed product was formed into tablets using a rotary tableting machine (HT-CVX-TYPEIII20, manufactured by HATA TEKKOSHO) to obtain uncoated tablets. The obtained uncoated tablets (900.6 g) were put into a film coating machine (HCT-30, manufactured by Freund Corporation) and film coated with a liquid prepared by dispersing or dissolving Opadry (registered trademark) QX in purified water, to obtain film coated tablets of Example 1.

<<Preparation of Tablets of Example 2>>

In accordance with the formulation described in Table 1, 165.75 g of gilteritinib hemifumarate, 186.15 g of mannitol, and 126.0 g of sucralose were mixed using a fluidized bed granulator (GPCG-1, manufactured by Powrex) (hereinafter referred to as GPCG-1), and the mixture was granulated by spraying 475 g of an isomalt hydrate aqueous solution (solid content: 10% by weight) as a binder, and dried to obtain a granulated product. After sieving to remove aggregates, 212.08 g was weighed from 401.9 g of the obtained granulated product, and 10.84 g of L-HPC and 3.23 g of Mg-St were added thereto and hand-mixed using a polyethylene bag to obtain a mixed product. The obtained mixed product was formed into tablets using a rotary tableting machine (EX-10, manufactured by HATA TEKKOSHO) to obtain uncoated tablets. The obtained uncoated tablets (37.69 g) were put into a film coating machine (MINI COATER/DRIER-2, manufactured by CALEVA) and film coated with a liquid prepared by dispersing or dissolving Opadry (registered trademark) QX in purified water, to obtain film coated tablets of Example 2.

Experimental Example 2

Each film coated tablet prepared in Referential Example, Comparative Example 1, Example 1, and Example 2 was put into a separate high-density polyethylene bottle, and allowed to stand at 40° C. and 75% RH for 1 month, 2 months, or 3 months, or at 70° C. for 9 days, to obtain each storage sample. In this connection, the sealing conditions were that the bottle mouth was sealed with an induction seal and the lid was closed, and the opening conditions were that the bottle was not covered. With respect to each storage sample, a dissolution test was carried out, using a dissolution tester (NTR-6100 series, NTR-6200 series, or NTR-6400 series, manufactured by TOYAMA SANGYO), in accordance with a Dissolution Test, a paddle method of the Japanese Pharmacopoeia, Seventeenth Edition using 900 mL of 0.1 mol/L hydrochloric acid as a dissolution test fluid at a paddle rotation speed of 50 rpm. After 15 minutes and 30 minutes from the start of the test, the peak area of gilteritinib in the dissolution test fluid was measured using an ultraviolet-visible spectrophotometric method (UV method) or a high performance liquid chromatography method (HPLC method), and the concentration of gilteritinib was calculated from the obtained peak area to calculate the dissolution rate. In the UV method, the measurement was carried out using an ultraviolet-visible spectrophotometer (UV-1800, manufactured by Shimadzu Corporation) (wavelength: 313 nm). In the HPLC method, the measurement was carried out using an Alliance HPLC (registered trademark) system (manufactured by Nihon Waters) (wavelength: 314 nm). The column used in the HPLC method was CAPCELL-PAK C18 AQ (inner diameter: 4.6 mm, length: 150 mm, particle size: 3 µm, manufactured by OSAKA SODA) or its equivalent. The column was used while maintaining it at 40° C., and perchloric acid solution (pH 2.2)/acetonitrile mixed liquid=65/35 was used as the mobile phase. The dissolution rate of gilteritinib in each sample without storage and each storage sample is shown in Table 2.

TABLE 2

| Storage conditions | | Referential Example | | Comparative Example 1 | | Example 1 | | Example 2 | |
|---|---|---|---|---|---|---|---|---|---|
| Period | Packaging form | 15 min. | 30 min. | 15 min. | 30 min. | 15 min. | 30 min. | 15 min. | 30 min. |
| Without storage | | 93 | 101 | 90.4 | 101.2 | 95.8 | 103.2 | 99.1 | 99.0 |
| 40° C. 75% RH 1 month | Sealed | 100 | 101 | — | — | 90.5 | 101.0 | 98.9 | 99.1 |
| 40° C. 75% RH 2 months | Sealed | — | — | 86.4 | 98.2 | — | — | 97.1 | 97.0 |
| 40° C. 75% RH 3 months | Sealed | 90 | 101 | 74.5 | 97.6 | 88.1 | 101.3 | — | — |
| 40° C. 75% RH 1 month | Opened | — | — | 83.4 | 104.3 | 94.9 | 103.2 | 97.5 | 97.6 |
| 40° C. 75% RH 2 months | Opened | — | — | 76.2 | 97.1 | — | — | 97.8 | 98.2 |
| 40° C. 75% RH 3 months | Opened | — | — | 76.9 | 99.4 | 94.2 | 102.2 | — | — |
| 70° C. 9 days | Sealed | — | — | 61.2 | 89.2 | 100.0 | 100.4 | 96.7 | 96.4 |

In the samples in which the tablet of Referential Example was stored at 40° C. and 75% RH under the sealing conditions for 1 month and 3 months, the dissolution rate of gilteritinib 15 minutes after the start of the test was 85% or more. On the other hand, in the samples in which the tablet of Comparative Example 1 was stored at 40° C. and 75% RH under the sealing conditions for 3 months, and at 70° C. under the sealing conditions for 9 days, the dissolution rate of gilteritinib 15 minutes after the start of the test was 75% or less. However, in Examples 1 and 2 in which the binder was isomalt hydrate, under all storage conditions, the dissolution rate of gilteritinib 15 minutes after the start of the test was 85% or more.

Formulations of Comparative Examples 2 to 3 and Examples 3 to 7

The formulation of Comparative Example 2 in which the type of film coating agent of Comparative Example 1 was changed, and the formulation of Comparative Example 3 without film coating are shown in Table 3. Furthermore, the formulation of Example 3 in which the sweetener of Example 1 was replaced with aspartame, and the formulations of Examples 4 to 7 in which isomalt hydrate of Example 1 was replaced with maltitol, sorbitol, sucrose, or trehalose are shown in Table 3.

TABLE 3

| Component | Comp. Ex. 2 | Comp. Ex. 3 | Ex. 3 | Ex. 4 | Ex. 5 | Ex. 6 | Ex. 7 |
|---|---|---|---|---|---|---|---|
| Gilteritinib hemifumarate | 11.05 | 11.05 | 11.05 | 11.05 | 11.05 | 11.05 | 11.05 |
| Mannitol | 12.625 | 12.625 | 10.43 | 10.43 | 10.43 | 10.43 | 10.43 |
| Sucralose | 8.0 | 8.0 | — | 8.4 | 8.4 | 8.4 | 8.4 |
| Aspartame | — | — | 8.4 | — | — | — | — |
| HPC | 1.05 | 1.05 | — | — | — | — | — |
| Isomalt hydrate | — | — | 3.6 | — | — | — | — |
| Maltitol | — | — | — | 3.6 | — | — | — |
| Sorbitol | — | — | — | — | 3.6 | — | — |
| Sucrose | — | — | — | — | — | 3.6 | — |
| Trehalose | — | — | — | — | — | — | 3.6 |
| L-HPC | 1.75 | 1.75 | 1.8 | 1.8 | 1.8 | 1.8 | 1.8 |
| Mg-St | 0.525 | 0.525 | 0.72 | 0.72 | 0.72 | 0.72 | 0.72 |
| Uncoated tablet | 35.0 | 35.0 | 36.0 | 36.0 | 36.0 | 36.0 | 36.0 |
| Opadry (registered trademark) QX | 1.05 | — | 1.1 | 1.1 | 1.1 | 1.1 | 1.1 |
| Film coated tablet | 36.05 | — | 37.1 | 37.1 | 37.1 | 37.1 | 37.1 |

Unit: mg

<<Preparation of Tablets of Comparative Example 2 and Comparative Example 3>>

In accordance with the formulations described in Table 3, 165.76 g of gilteritinib hemifumarate, 189.26 g of mannitol, and 119.988 g of sucralose were mixed using GPCG-1, and the mixture was granulated by spraying 225.0 g of an HPC aqueous solution (solid content: 7% by weight) as a binder, and dried to obtain a granulated product. After sieving to remove aggregates, 196.35 g was weighed from 296.83 g of the obtained granulated product, and 10.51 g of L-HPC and 3.15 g of Mg-St were added thereto, and mixed and formed into tablets by the same method as that in Example 2 to obtain uncoated tablets of Comparative Example 3. The obtained uncoated tablets (10.5152 g) were film coated by the same method as that in Example 2 to obtain film coated tablets of Comparative Example 2.

<<Preparation of Tablets of Example 3>>

In accordance with the formulation described in Table 3, 165.77 g of gilteritinib hemifumarate, 156.478 g of mannitol, and 126.028 g of aspartame were mixed using GPCG-1, and the mixture was granulated by spraying 270.0 g of an isomalt hydrate aqueous solution (solid content: 20% by weight) as a binder, and dried to obtain a granulated product. After sieving to remove aggregates, 267.85 g was weighed from 442.52 g of the obtained granulated product, and 14.43 g of L-HPC and 5.76 g of Mg-St were added thereto, and mixed and formed into tablets by the same method as that in Example 2 to obtain uncoated tablets. The obtained uncoated tablets (10.8147 g) were film coated by the same method as that in Example 2 to obtain film coated tablets of Example 3.

<<Preparation of Tablets of Example 4>>

In accordance with the formulation described in Table 3, 165.76 g of gilteritinib hemifumarate, 156.45 g of mannitol, and 126.02 g of sucralose were mixed using GPCG-1, and the mixture was granulated by spraying 270.0 g of a maltitol aqueous solution (solid content: 20% by weight) as a binder, and dried to obtain a granulated product. After sieving to remove aggregates, 267.85 g was weighed from 459.84 g of the obtained granulated product, and 14.40 g of L-HPC and 5.76 g of Mg-St were added thereto, and mixed and formed into tablets by the same method as that in Example 2 to obtain uncoated tablets. The obtained uncoated tablets (10.7941 g) were film coated by the same method as that in Example 2 to obtain film coated tablets of Example 4.

<<Preparation of Tablets of Example 5>>

In accordance with the formulation described in Table 3, 165.75 g of gilteritinib hemifumarate, 156.44 g of mannitol, and 126.02 g of sucralose were mixed using GPCG-1, and the mixture was granulated by spraying 270.0 g of a sorbitol aqueous solution (solid content: 20% by weight) as a binder, and dried to obtain a granulated product. After sieving to remove aggregates, 267.84 g was weighed from 425.03 g of the obtained granulated product, and 14.41 g of L-HPC and 5.76 g of Mg-St were added thereto, and mixed by the same method as that in Example 2, and formed into tablets using a manual tabletop tablet molding machine (HANDTAB-200, manufactured by Ichihashi Seiki) to obtain uncoated tablets. The obtained uncoated tablets (870.8 mg) were film coated by the same method as that in Example 2 to obtain film coated tablets of Example 5.

<<Preparation of Tablets of Example 6>>

In accordance with the formulation described in Table 3, 165.74 g of gilteritinib hemifumarate, 156.45 g of mannitol, and 126.00 g of sucralose were mixed using GPCG-1, and the mixture was granulated by spraying 270.2 g of a sucrose aqueous solution (solid content: 20% by weight) as a binder, and dried to obtain a granulated product. After sieving to remove aggregates, 267.84 g was weighed from 458.3 g of the obtained granulated product, and 14.41 g of L-HPC and 5.76 g of Mg-St were added thereto, and mixed and formed into tablets by the same method as that in Example 2, to obtain uncoated tablets. The obtained uncoated tablets (10.8116 g) were film coated by the same method as that in Example 2 to obtain film coated tablets of Example 6.

<<Preparation of Tablets of Example 7>>

In accordance with the formulation described in Table 3, 165.76 g of gilteritinib hemifumarate, 156.45 g of mannitol, and 126.03 g of sucralose were mixed using GPCG-1, and the mixture was granulated by spraying 270.0 g of a trehalose aqueous solution (solid content: 20% by weight) as a binder, and dried to obtain a granulated product. After sieving to remove aggregates, 267.84 g was weighed from 469.39 g of the obtained granulated product, and 14.42 g of L-HPC and 5.76 g of Mg-St were added thereto, and mixed and formed into tablets by the same method as that in Example 2, to obtain uncoated tablets. The obtained uncoated tablets (10.8207 g) were film coated by the same method as that in Example 2 to obtain film coated tablets of Example 7.

Experimental Example 3

Each film coated tablet or uncoated tablet prepared in Comparative Examples 2 to 3 and Examples 3 to 7 was put into a separate high-density polyethylene bottle, and allowed to stand at 40° C. and 75% RH for 1 month, 2 months, or 3 months, or at 70° C. for 9 days, to obtain each storage sample. With respect to each storage sample, a dissolution test was carried out under the same conditions as those in Experimental Example 2, and the dissolution rate was calculated. The dissolution rate of gilteritinib in each sample without storage and each storage sample is shown in Table 4.

TABLE 4

| | Dissolution test Elapsed time Dissolution rate (%) | | | | | | | | | | | | | |
|---|---|---|---|---|---|---|---|---|---|---|---|---|---|---|
| Storage conditions | Comparative Example 2 | | Comparative Example 3 | | Example 3 | | Example 4 | | Example 5 | | Example 6 | | Example 7 | |
| Period Packaging form | 15 min. | 30 min. | 15 min. | 30 min. | 15 min. | 30 min. | 15 min. | 30 min. | 15 min. | 30 min. | 15 min. | 30 min. | 15 min. | 30 min. |
| Without storage | 93.9 | 94.5 | 66.2 | 94.7 | 95.9 | 101.0 | 97.5 | 97.6 | 98.9 | 99.1 | 91.9 | 96.1 | 93.1 | 102.5 |
| 40° C. Sealed 75% RH 1 month | 81.8 | 94.8 | 62.8 | 92.6 | 92.2 | 99.4 | 87.9 | 96.1 | 99.3 | 99.8 | 86.8 | 97.6 | 98.0 | 102.6 |

TABLE 4-continued

| | | Dissolution test Elapsed time Dissolution rate (%) | | | | | | | | | | | | | |
|---|---|---|---|---|---|---|---|---|---|---|---|---|---|---|---|
| Storage conditions | | Comparative Example 2 | | Comparative Example 3 | | Example 3 | | Example 4 | | Example 5 | | Example 6 | | Example 7 | |
| Period | Packaging form | 15 min. | 30 min. | 15 min. | 30 min. | 15 min. | 30 min. | 15 min. | 30 min. | 15 min. | 30 min. | 15 min. | 30 min. | 15 min. | 30 min. |
| 40° C. 75% RH 2 months | Sealed | 74.8 | 92.7 | 61.6 | 91.4 | 95.5 | 100.2 | 82.9 | 96.8 | 100.6 | 100.9 | 92.0 | 97.1 | 96.6 | 101.1 |
| 40° C. 75% RH 3 months | Sealed | 77.6 | 93.9 | 64.9 | 92.0 | 93.9 | 99.1 | 81.7 | 96.9 | 98.7 | 98.7 | 85.6 | 95.2 | 95.0 | 100.2 |
| 40° C. 75% RH 1 month | Opened | 80.8 | 94.6 | 62.1 | 92.9 | 99.7 | 99.6 | 96.1 | 96.3 | 99.0 | 99.2 | 91.9 | 95.0 | 90.7 | 102.5 |
| 40° C. 75% RH 2 months | Opened | 75.5 | 94.0 | 61.8 | 91.8 | 99.3 | 100.0 | 96.8 | 96.9 | 99.1 | 99.3 | 93.0 | 96.3 | 97.3 | 101.5 |
| 40° C. 75% RH 3 months | Opened | 76.1 | 94.6 | 62.3 | 92.2 | 99.9 | 99.9 | 94.8 | 95.1 | 100.2 | 100.2 | 90.0 | 95.2 | 92.4 | 102.7 |
| 70° C. 9 days | Sealed | 82.2 | 93.7 | 61.7 | 90.6 | 45.6 | 74.8 | 94.7 | 98.6 | 98.2 | 101.9 | 89.2 | 93.1 | 100.2 | 101.3 |

In the samples in which the tablets of Comparative Examples 2 to 3 were stored at 40° C. and 75% RH under the sealing conditions or the opening conditions for 2 months and 3 months, the dissolution rate of gilteritinib 15 minutes after the start of the test was 80% or less. However, in Examples 4 to 7 in which the binder was sugars and/or sugar alcohols, under all storage conditions, the dissolution rate of gilteritinib 15 minutes after the start of the test was 80% or more. Furthermore, in the samples in which the tablet of Example 3 in which the binder was sugars and/or sugar alcohols was stored at 40° C. and 75% RH under the sealing conditions or the opening conditions for 2 months and 3 months, the dissolution rate of gilteritinib 15 minutes after the start of the test was 80% or more.

From the above results, by containing two or more kinds of sugars and/or sugar alcohols, a pharmaceutical composition comprising gilteritinib or a pharmaceutically acceptable salt thereof and a sweetener that reduces bitterness, and having excellent dissolution stability can be provided.

INDUSTRIAL APPLICABILITY

According to the present invention, a pharmaceutical composition suppressing the decrease in dissolution stability over time, comprising gilteritinib or a pharmaceutically acceptable salt thereof and a sweetener that reduces bitterness, and exhibiting excellent dissolution stability can be provided.

Although the present invention has been described with reference to specific embodiments, various changes and modifications obvious to those skilled in the art are possible without departing from the scope of the appended claims.

The invention claimed is:

1. A pharmaceutical composition comprising 6-ethyl-3-{3-methoxy-4-[4-(4-methylpiperazin-1-yl) piperidin-1-yl] anilino}-5-[(oxan-4-yl) amino] pyrazine-2-carboxamide or a pharmaceutically acceptable salt thereof, a sweetener, and two or more sugars and/or sugar alcohols.

2. The pharmaceutical composition according to claim 1, wherein the sweetener is one, or two or more compounds selected from the group consisting of saccharin, acesulfame potassium, aspartame, and sucralose, and a mixture thereof.

3. The pharmaceutical composition according to claim 1, wherein the sweetener is sucralose.

4. The pharmaceutical composition according to claim 1, wherein the sugars are disaccharides and the sugar alcohols have 6 or 12 carbon atoms.

5. The pharmaceutical composition according to claim 1, wherein the two or more sugars and/or sugar alcohols are selected from the group consisting of mannitol, isomalt hydrate, maltitol, sorbitol, lactose, sucrose, and trehalose, and a mixture thereof.

6. The pharmaceutical composition according to claim 1, wherein one of the two or more sugars and/or sugar alcohols is mannitol.

7. The pharmaceutical composition according to claim 1, wherein one of the two or more sugars and/or sugar alcohols is selected from the group consisting of isomalt hydrate, maltitol, sorbitol, sucrose, and trehalose.

8. The pharmaceutical composition according to claim 1, wherein one of the two or more sugars and/or sugar alcohols is isomalt hydrate.

9. The pharmaceutical composition according to claim 7, wherein a content of the one of the two or more sugars and/or sugar alcohols with respect to a weight of the pharmaceutical composition is 1% by weight to 20% by weight.

10. The pharmaceutical composition according to claim 7, wherein the one of the two or more sugars and/or sugar alcohols is used as a binder.

11. The pharmaceutical composition according to claim 1, wherein the pharmaceutically acceptable salt thereof is a hemifumarate.

12. The pharmaceutical composition according to claim 1, wherein the pharmaceutical composition is solid.

13. The pharmaceutical composition according to claim 1, further comprising a disintegrating agent.

14. The pharmaceutical composition according to claim 12, wherein the pharmaceutical composition is a tablet.

15. The pharmaceutical composition according to claim 1, wherein the pharmaceutical composition is dissolved or dispersed in a suitable solvent, and is a solution, suspension, paste, or gel.

* * * * *